United States Patent [19]
Bierer et al.

[11] Patent Number: 5,811,568
[45] Date of Patent: Sep. 22, 1998

[54] PROCESS FOR THE PREPARATION OF MONO- AND BIS(PHOSPHOCHOLINE) DERIVATIVES WHICH HAVE ANTIFUNGAL ACTIVITY

[75] Inventors: Donald E. Bierer; Jeffrey M. Dener, both of Daly City; Thien V. Truong, Emeryville, all of Calif.

[73] Assignee: Shaman Pharmaceuticals, Inc., South San Francisco, Calif.

[21] Appl. No.: 234,483

[22] Filed: Apr. 28, 1994

(Under 37 CFR 1.47)

Related U.S. Application Data

[63] Continuation-in-part of PCT/US93/09623, Oct. 8, 1993, which is a continuation-in-part of Ser. No. 95,016, Oct. 8, 1992, abandoned.

[51] Int. Cl.$^6$ ........................................................ C07F 9/02
[52] U.S. Cl. .................................................................. 558/87
[58] Field of Search .................................. 536/124, 94.1; 558/871, 87

[56] References Cited

U.S. PATENT DOCUMENTS

| | | | |
|---|---|---|---|
| 4,408,052 | 10/1983 | Hozumi et al. | 546/22 |
| 4,595,681 | 6/1986 | Snyder et al. | |
| 4,684,625 | 8/1987 | Eppstein et al. | 514/19 |
| 4,725,588 | 2/1988 | Snyder et al. | |
| 5,087,721 | 2/1992 | Counsell et al. | |

FOREIGN PATENT DOCUMENTS

| | | |
|---|---|---|
| 0 050 460 | 10/1981 | European Pat. Off. |
| 0 138 559 | 10/1984 | European Pat. Off. |
| 38 29 899 | 9/1988 | Germany |
| 58-035194 | 3/1983 | Japan |
| 58-170792 | 10/1983 | Japan |
| WO 94/08563 | 4/1994 | WIPO |

OTHER PUBLICATIONS

De Boer et al., 1976, "The Structure of Teichoic Acid from *Bacillus subtilis* var. niger WM as Determined by $^{13}$C Nuclear–Magnetic–Resonance Spectroscopy", Eur. J. Biochem. 62:1–6.

Ogawa et al., 1979, "Synthesis of the Repeating Unit of the Teichoic Acid Isolated from the Cell Wall of *Bacillus subtilis* VAR. niger WM", Carbohydrate Research 70:37–46.

Tsushima et al., 1982, "Syntheses and Antimicrobial Activities of Alkyl Lysophospholipids", Chem. Pharm. Bull. 30:3260–3270.

van Boeckel et al., 1983, "Synthesis of a Teichoic Acid Fragment of *Bacillus subtilis* Using a Modified Phosphotriester approach", Recl. Trav. Chim. Pays–Bas 102:526–537.

van Boeckel and van Boom, 1979, "Synthesis of glucosylphosphatidylglycerol via a phosphotriester intermediate", Tetrahedron Letters 37:3561–3564.

*Primary Examiner*—Elli Peselev
*Attorney, Agent, or Firm*—Pennie & Edmonds LLP

[57] ABSTRACT

This invention pertains to a synthetic process for obtaining a unique phosphocholine derivative which has been isolated from the leaves of the plant *Irbachia alata*, identified to be 1,22-bis[2-(trimethylammonium)ethylphosphatyl] docosane is disclosed. Also disclosed is a synthetic process for obtaining a novel class of mono- and bis(phosphocholine) derivatives which are useful as antiinfective agents. The compounds are particularly effective in treating fungal infections, especially those caused by *Candida albicans*, *Cryptococcus neoformans*, and *Aspergillus fumigatus*.

15 Claims, 3 Drawing Sheets

FIG. 1

X is OH, NH$_2$, NHR$_{15}$, or SH
X is OH, NH$_2$, NHR$_{15}$, or SH
E$_1$ is Br, Cl, I, F, or alternative leaving group
E$_2$ is Br, Cl, I, F, or alternative leaving group
PG is a protecting group, if needed
T, Q, V$_1$, V$_2$, F$_1$, F$_2$, R$_{61}$ and R$_{62}$ are as defined in section 3

PROCESS FOR THE PREPARATION OF MONO- AND BIS(PHOSPHOCHOLINE) DERIVATIVES WHICH HAVE ANTIFUNGAL ACTIVITY

This application is a continuation-in-part of International Application PCT/US93/09623, filed Oct. 8, 1993 which in turn is a continuation-in-part of application Ser. No. 07/950,416 filed Oct. 8, 1992, now abandoned, the entire disclosures of which are incorporated by reference herein in their entirety.

TABLES OF CONTENTS
1. FIELD OF INVENTION
2. BACKGROUND OF INVENTION
3. SUMMARY OF INVENTION
4. BRIEF DESCRIPTION OF THE FIGURES
5. DETAILED DESCRIPTION OF THE INVENTION
   5.1. SYNTHESIS OF THE PHOSPHOCHOLINE DERIVATIVES 2
   5.2. COMPOUNDS
   5.3. METHODS OF USE
6. EXAMPLES: SYNTHESIS OF PHOSPHOCHOLINES
   6.1. GENERAL EXPERIMENTAL MATERIALS AND METHODS
   6.2. EXAMPLES OF SYNTHESIS
7. ANTIFUNGAL ACTIVITY

1. FIELD OF INVENTION

This invention relates to a new class of phosphocholine derivatives as well as to a new synthetic process for preparing these compounds. The glycosylated phosphocholine derivatives of this invention exhibit substantial antifungal activity in slowing fungal growth and/or in killing fungi.

2. BACKGROUND OF INVENTION

The plant species *Irlbachia alata* has been used as an anti-infective agent in the Peruvian Amazon region. The leaves are squeezed and the liquid is applied to infected skin sores. The same liquid from the leaves is applied to skin problems and skin fungal infections. It is also used to treat vaginal yeast infections.

*Irlbachia alata* is a member of the plant family Gentianaceae. Species of this plant family occur in tropical South America, especially in the Amazon and Negro River basins. The plants in the genus Irlbachia are generally low herbs characteristically with 3–5 plinerved leaves, with the most consistent feature of this genus being its pollen morphology.

U.S. patent application Ser. No. 07/958,416 filed Oct. 8, 1992 describes a unique phosphocholine derivative which has been isolated from the leaves of the plant Irbachia alata, as well as a process for its isolation. International application PCT/US93/09623, filed Oct. 8, 1993 describes several classes of novel phosphocholine derivatives having antifungal activity. An object of the present invention is to provide a novel synthetic method to obtain the phosphocholine derivative isolated from *Irlbachia alata*, as well as to provide a synthetic method to obtain a whole class of phosphocholines, as well as their synthetic analogs, having an antifungal activity.

Citation or identification of any reference in Section 2 of this application shall not be construed as an admission that such reference is available as prior art to the present invention.

3. SUMMARY OF INVENTION

We have discovered a new method to synthesize the novel bis(phosphocholine) identified in U.S. patent application Ser. No. 07/958,416 filed on Oct. 8, 1992 and have discovered a new general synthetic process to obtain not only that phosphocholine, but also a whole class of phosphocholine derivatives. This class of phosphocholines has unique antifungal activity.

The class of phosphocholine derivatives having antifungal activity is defined by the following structure:

where Q is defined as:

$R_1$, $R_2$, $R_3$, $R_4$, $R_5$, and $R_6$ can independently be hydrogen, or an alkyl radical comprising 1 to 6 carbon atoms;

$A_1$ and $B_1$ are independent of each other and not necessarily equal to each other, but in some instances can be equal to each other, and $A_1$ and $B_1$ are defined as follows:

$A_1$ can be defined as oxygen, sulfur, C=O, nil, or $NR_7R_8$, where $R_7$ and $R_8$ can independently be hydrogen, an alkyl radical comprising 1 to 6 carbon atoms, or a protecting group as described in "Protecting Groups in Organic Synthesis" by Theodora Green and Peter G. M. Wuts; John Wiley and Sons, New York, 1991 (Green et al.);

$B_1$ can be defined as oxygen, sulfur, C=O, nil, or $NR_9R_{10}$, where $R_9$ and $R_{10}$ can independently be hydrogen, an alkyl radical comprising 1 to 6 carbon atoms, or a protecting group as described in Green et al.;

$m_1$, $n_1$, and $o_1$ are integers 0–40 according to the following criteria:

(1) $m_1$ can be 0 only if $A_1$ is nil and $n_1$, does not equal 0, or if $A_1$ is a phenyl, polylphenyl, heteroaromatic, or poly(heteroaromatic) ring as defined below;

(2) $o_1$ can be 0 only if $B_1$ is nil and $n_1$ does not equal 0, or if $A_1$ is a phenyl, polyphenyl, heteroaromatic, or poly(heteroaromatic) ring as defined below;

(3) $n_1$ cannot be 0 if $A_1$ and $B_1$ are both oxygen or if $A_1$ is oxygen and $B_1$ is either sulfur or $NR_9R_{10}$, and (4) the sum of $m_1+n_1+o_1$ is less than or equal to 40;

$A_1$ and can also be defined as:

where $R_{11}$ and $R_{12}$ can independently be hydrogen or an alkyl radical comprising 1 to 6 carbon atoms;

where the stereochemistry about the olefinic double bond can be either cis, trans, or a mixture of cis and trans isomers, and $p_1$ and $q_1$ are integers from 1 to 6, such that the sum of $m_1+n_1+o_1+[(p_1+q_1+p_2+q_2)2]$ is less than or equal to 40, where $p_2$ and $q_2$ are defined below; or $A_1$ can also be defined as one of the following structures:

where

$J_1$, $K_1$, $L_1$, and $M_1$ can be the same or different, or optionally interchanged, and are defined to be N or C—H, where the substitution pattern may be ortho, meta, or para with the provisio that the substituent is attached to a carbon atom;

$r_1$ is an integer 0 to 6, and $s_1$ is an integer 0 to 6.

The phrase "a variable is an integer x to y" is intended to mean the variable can be an integer equal to x, between x and y or equal to y.

$B_1$ can also be defined as:

where $R_{13}$ and $R_{14}$ can independently or interchangeably be hydrogen or an alkyl radical comprising 1 to 6 carbon atoms;

where the stereochemistry about the olefinic double bond can be either cis, trans, or a mixture of cis and trans isomers, and $p_2$ and $q_2$ are integers 1 to 6, such that the sum of $m_1+n_1+o_1+[(p_1+q_1+p_2+q_2)2]$ is less than or equal to 40, where $p_1$ and $q_1$ were defined above; or $B_1$ can also be defined as one of the following structures:

or where $J_2$, $K_2$, $L_2$ and $M_2$ can be the same or different, or optionally interchanged, and are defined to be N or C—H, where the substitution pattern may be ortho, meta, or para with the provisio that the substituents are attached to a carbon atom;

$r_2$ is an integer 0 to 6, and $s_2$ is an integer 0 to 6.

X can be oxygen, sulfur, or $NR_{15}$, where $R_{15}$ can be hydrogen, an alkyl radical comprising 1 to 6 carbon atoms, phenyl, phenylmethyl, or a protecting group as described by Green et al;

Y can be oxygen, sulfur, or $NR_{16}$, where $R_{16}$ can be hydrogen, an alkyl radical comprising 1 to 6 carbon atoms, phenyl, phenylmethyl, or a protecting group as described by Green et al.

$W_1$ is $P(—OR_{17})$ (with $R_{17}$ being phenyl, phenylmethyl, hydrogen, or nil);

$W_2$ is $P(—OR_{18})$ (with $R_{18}$ being phenyl, phenylmethyl, hydrogen, or nil);

$Z_1$ is oxygen or sulfur;

$Z_2$ is oxygen or sulfur;

$D_1$ is oxygen;

$F_1$ is defined as:

$R_{19}$, $R_{20}$, $R_{21}$, $R_{22}$, $R_{23}$, and $R_{24}$ can independently or interchangeably be hydrogen, or an alkyl radical comprising 1 to 6 carbon atoms;

$G_1$ is defined to be oxygen, sulfur, C=O, nil, or $NR_{25}R_{26}$, where $R_{25}$ and $R_{26}$ can independently or interchangeably be hydrogen, an alkyl radical comprising 1 to 6 carbon atoms, phenyl, phenylmethyl, or a protecting group as described by Green et al.; or $G_1$ can also be:

, where the substitution pattern may be ortho, meta, or para;

$H_1$ is independent of $G_1$ and is defined to be oxygen, sulfur, C=O, nil, or $NR_{27}R_{28}$, where $R_{27}$ and $R_{28}$ can independently or interchangeably be hydrogen, an alkyl radical comprising 1 to 6 carbon atoms, phenyl, phenylmethyl, or a protecting group as described by Green et al.; and $a_1$, $b_1$, and $c_1$ are integers 0 to 20 according to the following criteria:

(1) $a_1$ can be 0 only if $G_1$ is nil and $b_1$ does not equal 0; or $a_1$ can be 0 if $G_1$ is substituted phenyl as defined above, (2) $c_1$ can be 0 only if $H_1$ is nil and $b_1$ does not equal 0; or $a_1$ can be 0 if $G_1$ is substituted phenyl as defined above,

(3) $b_1$ cannot be 0 if $G_1$ and $H_1$ are both oxygen or if $G_1$ is oxygen and $H_1$ is either sulfur or $NR_{27}R_{28}$, and (4) the sum of $a_1+b_1+c_1$ is less than or equal to 20;

$G_1$ can also be defined as:

or

, where where $R_{29}$ and $R_{30}$ can independently or interchangeably be hydrogen or an alkyl radical comprising 1 to 6 carbon atoms;

where the stereochemistry about the olefinic double bond can be either cis, trans, or a mixture of cis and trans isomers, and $u_1$ and $v_1$ are integers from 1 to 6, such that the sum of $a_1+b_1+c_1+[(u_1+v_1+w_1+z_1)2]$ ($w_1$ and $z_1$ are defined below) is less than or equal to 20;

$H_1$ can also be defined as:

or

, where where $R_{31}$ and $R_{32}$ can independently or interchangeably be hydrogen or an alkyl radical comprising 1 to 6 carbon atoms;

where the stereochemistry about the olefinic double bond can be either cis, trans, or a mixture of cis and trans isomers, and $w_1$ and $z_1$ are integers from 1 to 6, such that the sum of $a_1+b_1c_1+[(u_1+v_1+w_1+z_1)2]$ is less than or equal to 20;

$H_1$ can also be defined as:

, where the substitution pattern may be ortho, meta, or para;

$D_2$ is oxygen;

$F_2$ is defined as:

where $R_{33}$, $R_{34}$, $R_{35}$, $R_{36}$, $R_{37}$, and $R_{38}$ can independently or interchangeably be hydrogen, or an alkyl radical comprising 1 to 6 carbon atoms;

$G_2$ is defined to be oxygen, sulfur, C=O, nil, or $NR_{39}R_{40}$, where $R_{39}$ and $R_{40}$ can independently or interchangeably be hydrogen, an alkyl radical comprising 1 to 6 carbon atoms, phenyl, phenylmethyl, or a protecting group as described by Green et al.; or $G_2$ can also be:

where the substitution pattern may be ortho, meta, or para;

$H_2$ is independent of $G_2$ and is defined to be oxygen, sulfur, C=O, nil, or $NR_{41}R_{42}$, where $R_{41}$ and $R_{42}$ can independently or interchangeably be hydrogen, an alkyl radical comprising 1 to 6 carbon atoms, phenyl, phenylmethyl, or a protecting group as described by Green et al.; and $a_2$, $b_2$, and $c_2$ are integers between 0 and 20 according to the following criteria:

(1) $a_2$ can be 0 only if $G_2$ is nil and $b_2$ does not equal 0, or $a_2$ can be 0 if $G_2$ is substituted phenyl as described above;

(2) $c_2$ can be 0 only if H2 is nil and $b_2$ does not equal 0, or $a_2$ can be 0 if $G_2$ is substituted phenyl as described above;

(3) $b_2$ cannot be 0 if $G_2$ and $H_2$ are both oxygen or if $G_2$ is oxygen and $H_2$ is either sulfur or $NR_{41}R_{42}$, and (4) the sum of $a_2+b_2+c_2$ is less than or equal to 20;

$G_2$ can also be defined as:

, where where $R_{43}$ and $R_{44}$ can independently or interchangeably be hydrogen or an alkyl radical comprising 1 to 6 carbon atoms;

where the stereochemistry about the olefinic double bond can be either cis, trans, or a mixture of cis and trans isomers, and $u_2$ and $v_2$ are integers from 1 to 6, such that the sum of $a_2+b_2+c_2+[(u_2+v_2+w_2+z_2)2]$ ($w_2$ and $z_2$ are defined below) is less than or equal to 20;

$H_2$ can also be defined as:

where
where $R_{45}$ and $R_{46}$ can independently or interchangeably be hydrogen or an alkyl radical comprising 1 to 6 carbon atoms;
where the stereochemistry about the olefinic double bond can be either cis, trans, or a mixture of cis and trans isomers,
and $w_2$ and $z_2$ are integers from 1 to 6, such that the sum of $a_2+b_2+c_2+[(u_2+v_2+w_2+z_2)2]$ is less than or equal to 20.

$H_2$ can also be:

where the substitution pattern may be ortho, meta, or para;

$V_1$ is $NR_{47}R_{48}R_{49}$, where $R_{47}$, $R_{48}$, and $R_{49}$ can independently or interchangeably be hydrogen or alkyl radicals of C1 to C20 chain length which optionally possess 1 to 4 olefin or alkynyl unsaturation units, or mixtures or combinations thereof; where $R_{47}$ and $R_{48}$ can be part of a ring containing 2 to 8 carbon atoms, or part of an aromatic or heteroaromatic; or where $R_{47}$, $R_{48}$, and $R_{49}$ can be part of a bridged alkyl ring; or $R_{49}$ can be:

—$(CH_2)_{d1}$—$R_{50}$ or nil, where $d_1=0$ to 20 and where $R_{50}$ is defined as hydrogen, a cycloalkyl radical of 3 to 8 carbon atoms, an aryl or optionally substituted aryl radical, a pyridyl or optionally substituted pyridyl radical, a furanyl or optionally substituted furanyl radical, a thiophenyl or optionally substituted thiophenyl radical, or a pyrollyl or optionally substituted pyrollyl radical, or when $d_1 \neq 0$ or 1, then $R_{50}$ can be SH, $SO_3H$, $SO_3^-$, COOH, $COO^-$, $NH_2$, $NH_3^+$, or OH;

$V_2$ is $NR_{51}R_{52}R_{53}$, where $R_{51}$, $R_{52}$, and $R_{53}$ can independently or interchangeably be hydrogen or an alkyl radicals of C1 to C20 chain length which optionally possess 1 to 4 olefin or alkynyl unsaturation units, or mixtures or combinations thereof; where $R_{51}$ and $R_{52}$ can be part of a ring containing 2 to 8 carbon atoms, or part of an aromatic or heteroaromatic; or where $R_{51}$, $R_{52}$, and $R_{53}$ can be part of a bridged alkyl ring; or $R_{53}$ can be:

—$(CH_2)_{d2}$—$R_{54}$ or nil, where $d_2=0$ to 20 and where $R_{54}$ is defined as hydrogen, a cycloalkyl radical of 3 to 8 carbon atoms, an aryl or optionally substituted aryl radical, a pyridyl or optionally substituted pyridyl radical, a furanyl or optionally substituted furanyl radical, a thiophenyl or optionally substituted thiophenyl radical, or a pyrollyl or optionally substituted pyrollyl radical, or when $d_2 \neq 0$ or 1, then $R_{54}$ can be SH, $SO_3H$, $SO_3^-$, COOH, $COO^-$, $NH_2$, $NH_3^+$, or OH;

wherein $V_1$ or $V_2$ or both must be an amine (i.e. $NR_{47}R_{48}R_{49}$; $NR_{51}R_{52}R_{53}$)

A preferred subgroup of the above described class of phosphocholine derivatives have the following structure:

where
T is defined as Br, Cl, F, I, $NH_2$, $NHNH_2$, OH, $SO_3H$, $PO_3H$, SH, $N_3$, COOH, SH, $NHNR_{55}R_{56}$, $COOR_{57}$, or $SR_{58}$, $S(O)_{t1}R_{58}$, $OR_{59}$, $S(O)_{t1}NR_{55}R_{56}$, or $NR_{51}R_{52}$, $R_{53}$;

where $R_{51}$, $R_{52}$, and $R_{53}$ are defined above;
$R_{55}$ and $R_{56}$ can be the same or different, or independent or optionally interchanged, and defined to be hydrogen, methyl, ethyl, n-propyl, isopropyl, isobutyl, t-butyl, cyclopropyl, phenyl, phenylmethyl, an alkyl radical containing 1 to 20 carbon atoms which can optionally possess one to four, olefinic or alkynyl unsaturations, or combinations or mixtures thereof, or a protecting group as described by Green et al.;

$R_{57}$ is hydrogen, methyl, ethyl, n-propyl, isopropyl, isobutyl, t-butyl, cyclopropyl, phenyl, phenylmethyl, an alkyl radical containing 1 to 20 carbon atoms which can optionally possess one to four, olefinic or alkynyl unsaturations, or a protecting group as described by Green et al.;

$R_{58}$ can be hydrogen, methyl, ethyl, n-propyl, isopropyl, isobutyl, t-butyl, cyclopropyl, phenyl, phenylmethyl, optionally substituted phenyl, optionally substituted phenylmethyl, an alkyl radical containing 1 to 20 carbon atoms which can optionally possess one to four, olefinic or alkynyl unsaturations, or combinations or mixtures thereof, or a protecting group and described by Green et al.;

$R_{59}$ can be hydrogen, methyl, ethyl, n-propyl, isopropyl, isobutyl, t-butyl, cyclopropyl, phenyl, phenylmethyl, an alkyl radical containing 1 to 20 carbon atoms which can optionally possess one to four, olefinic or alkynyl unsaturations, or combinations or mixtures thereof, an acyl moiety of the type or a protecting group as described by Green et al.;
where
$R_{60}$ is hydrogen, methyl, ethyl, n-propyl, isopropyl, isobutyl, t-butyl, cyclopropyl, phenyl, phenylmethyl, an alkyl chain of C4 to C20 chain length, or a protecting group and described by Green et al.; and
$t_1$ is 0, 1, or 2.
$R_{61}$ is defined as phenyl, phenylmethyl, hydrogen, or nil;
$R_{62}$ is defined as phenyl, phenylmethyl, hydrogen, or nil; and
where X, Y, Q, $F_1$, $F_2$, $V_1$ and $V_2$, are defined above.

Another preferred subgroup of the above described class of phosphocholine derivatives have the following structure:

where
T, $R_{61}$, $R_{62}$, Q, $F_1$, $F_2$, $V_1$, and $V_2$ are defined above, and where $R_{51}$, $R_{52}$, $R_{53}$, $R_{55}$, $R_{56}$, $R_{57}$, $R_{58}$, $R_{59}$, and $t_1$ are defined above.

Another preferred subgroup of the above described class of phosphocholine derivatives have the following structure:

where $R_{63}$, $R_{64}$, and $R_{65}$ can independently or interchangeably be hydrogen or an alkyl radical of C1 to C20 chain length which optionally possesses 1 to 4 olefin or alkynyl unsaturation units, or mixtures or combinations thereof;

where $R_{63}$ and $R_{64}$ can be part of a ring containing 2 to 8 carbon atoms, or part of an aromatic or heteroaromatic ring; or where $R_{63}$, $R_{64}$, and $R_{65}$ can be part of a bridged alkyl ring; or $R_{65}$ can be:

—$(CH_2)_e$—$R_{66}$ or nil, where e=0 to 20 and where $R_{66}$ is defined as hydrogen, a cycloalkyl radical of 3 to 8 carbon atoms, an aryl or optionally substituted aryl radical, a pyridyl or optionally substituted pyridyl radical, a furanyl or optionally substituted furanyl radical, a thiophenyl or optionally substituted thiophenyl radical, or a pyrollyl or optionally substituted pyrollyl radical, or when e≠0 or 1, then $R_{66}$ can be SH, $SO_3H$, $SO_3^-$, COOH, COO$^-$, $NH_2$, $NH_3^+$, or OH.

The preferred protecting groups for alcoholic functions are among but not exclusive to the following: acetate, benzoate, benzyl, benzylidine, isopropylidine, tert-butyldimethylsilyl, tert-butyldiphenylsilyl, allyl, methoxyethoxyethyl, triphenylmethyl, tetrahydropyranyl, diphenylmethyl, p-methoxybenzyl, 3,4-dimethoxybenzyl, p-toluenesulfonyl, benzenesulfonyl, tert-butyl, tert-butyloxymethyl, 2-(trimethylsilyl)ethoxymethyl, methoxymethyl, 2-(trimethylsilyl)ethyl, dimethylthexylsilyl, benzyloxymethyl, p-methoxybenzyloxymethyl, (4-methoxyphenoxy)methyl, methylthiomethyl, 2,2,2-trichloroethoxy-methyl, tribenzylsilyl, triphenylsilyl, diphenylmethylsilyl, and tert-butylmethoxyphenylsilyl.

The preferred protecting groups for nitrogen are among but not exclusive to the following: tert-butyloxycarbonyl, benzyloxycarbonyl, 9-phenylfluorenyl, allyloxycarbonyl, allyl, benzyl, triphenylmethyl, adamantyloxycarbonyl, 2,2,2-trichloroethyloxycarbonyl, 2-(trimethylsilyl)ethoxycarbonyl, p-toluenesulfonyl, benzylidine, diphenylmethyloxycarbonyl, 2-cyanoethyl, 2-cyanoethyloxycarbonyl, 9-fluorenylmethyloxycarbonyl, p-methoxybenzyloxycarbonyl, p-nitrobenzyloxycarbonyl, p-bromobenzyloxycarbonyl, benzenesulfonyl, toluenesulfonyl, p-chlorobenzyloxycarbonyl, o-nitrobenzyloxycarbonyl, benzylidine, N-1,1-dithiomethylene, 2,3,6-trimethyl-4-methoxybenzenesulfonyl, benzylsulfonyl, 2,4,6-trimethoxybenzenesulfonyl, 2,4,6-trimethylbenzenesulfonyl, p-methoxybenzenesulfonyl, and 2-trimethylsilylethanesulfonyl.

The preferred protecting groups for carboxyl oxygen are among but not exclusive to the following: methyl, ethyl, isopropyl, t-butyl, diphenylmethyl, benzyl, 2-cyanoethyl, 2-(trimethylsilyl)ethyl, 2,2,2-trichloroethyl, tert-butyldimethylsilyl, tert-butyldiphenylsilyl, 2-(trimethylsilyl)ethoxymethyl, tribenzylsilyl, triphenylsilyl, diphenylmethylsilyl, tert-butylmethoxyphenylsilyl, p-methoxybenzyl, and phenacyl.

The preferred protecting groups for sulfur are among but not exclusive to the following: triphenylmethyl, tert-butyl, acetyl, benzyl, p-methoxybenzyl, p-nitrobenzyl, diphenylmethyl, 1-adamantyl, and 2-cyanoethyl.

4. BRIEF DESCRIPTION OF THE FIGURES

The present invention may be understood more fully by reference to the following detailed description, examples of specific embodiments of the invention and the appended figures in which.

5. DETAILED DESCRIPTION OF THE INVENTION

The phosphocholine derivatives described in this invention are prepared by synthetic methods outlined below.

5.1. SYNTHESIS OF THE PHOSPHOCHOLINE DERIVATIVES

A versatile synthetic method has been developed to synthesize the mono and bis(phosphocholine) derivatives of this invention. The general synthesis method is outlined in FIG. 1.

Figure 1:
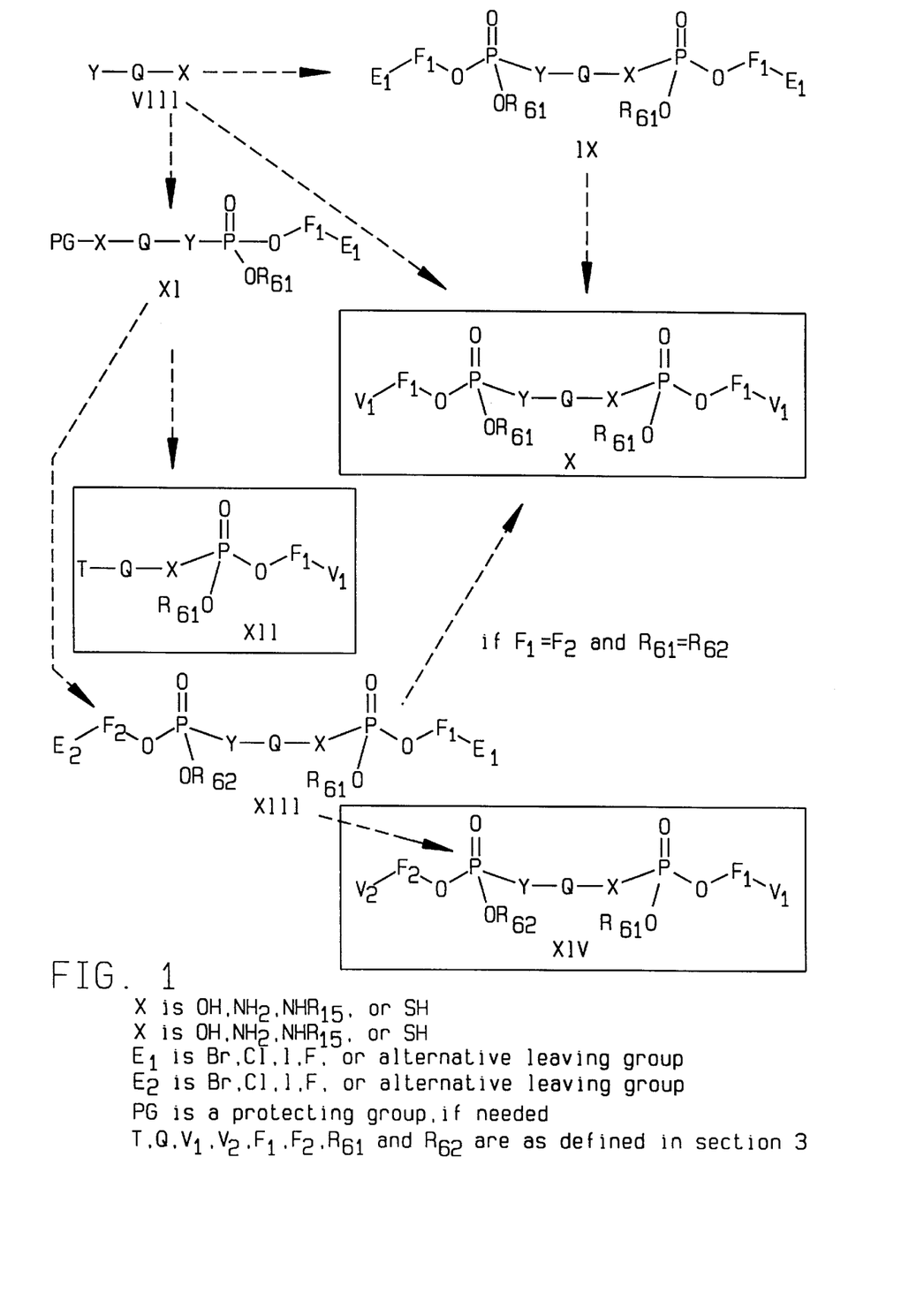
FIG. 1 schematically outlines the general schemes for the synthesis of mono and bis(phosphocholines) according to the method(s) of the invention.

In general, the process begins with a bifunctional alcohol, thiol or amine, e.g. Y—Q—X (VIII). Functional group X is generally protected with a protecting group (PG) and then the remaining functional group Y is phosphorylated using a phosphorylating agent of the type to provide a monophosphate XI. $F_1$ is defined as above, and $E_1$ is a leaving group selected from the group consisting of benzenesulfonyl, pentafluorobenzenesulfonyl, toluenesulfonyl, p-nitrobenzenesulfonyl, p-bromobenzenesulfonyl, p-chlorobenzenesulfonyl, p-iodobenzenesulfonyl, p-fluorobenzenesulfonyl, 2,4,6-trimethylbenzenesulfonyl, 2,4,6-triisopropylbenzenesulfonyl, methanesulfonyl, trifluoromethanesulfonyl, Br, Cl, I, and F.

Figure 2:
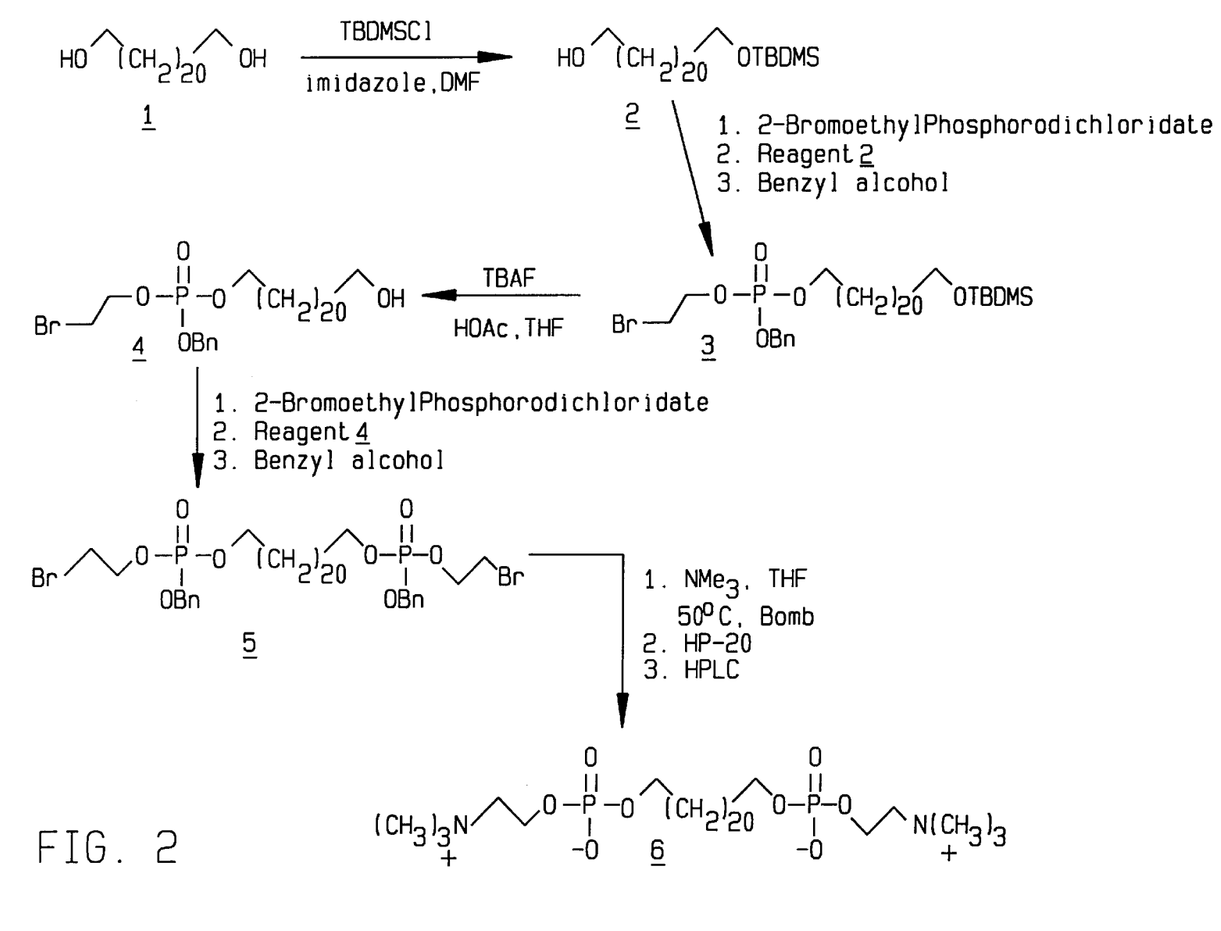
FIG. 2 schematically illustrates the step-wise synthesis of a bis-phosphocholine according to the invention using the synthesis of 1,22-bis[2-(trimethylammonium)ethylphosphatyl] docosane as an illustrative example.

Monophosphate XI can then be converted to a monophosphocholine derivative XII by displacing the leaving group $E_1$ with an amine, defined above as $V_1$, or $V_2$, and deprotecting the functional group X and converting X to T. Alternatively, monophosphate XI can be phosphorylated a second time with either the same, or different, phosphorylating agent, to provide either the symmetrical or unsymmetrical bisphosphate derivative, IX or XIII, respectively. Depending on the leaving groups $E_1$ and $E_2$, bis phosphate XIII can be converted to the desired unsymmetrical bis (phosphocholine) XIV simultaneously or in two separate steps by simultaneous or sequential displacement of $E_1$ and $E_2$ with $V_1$ and $V_2$. This reaction route by design can also be used to prepare symmetrical bis(phosphocholine) derivatives, such as X. An example of such a "step-wise" process is illustrated in FIG. 2.

Figure 3:
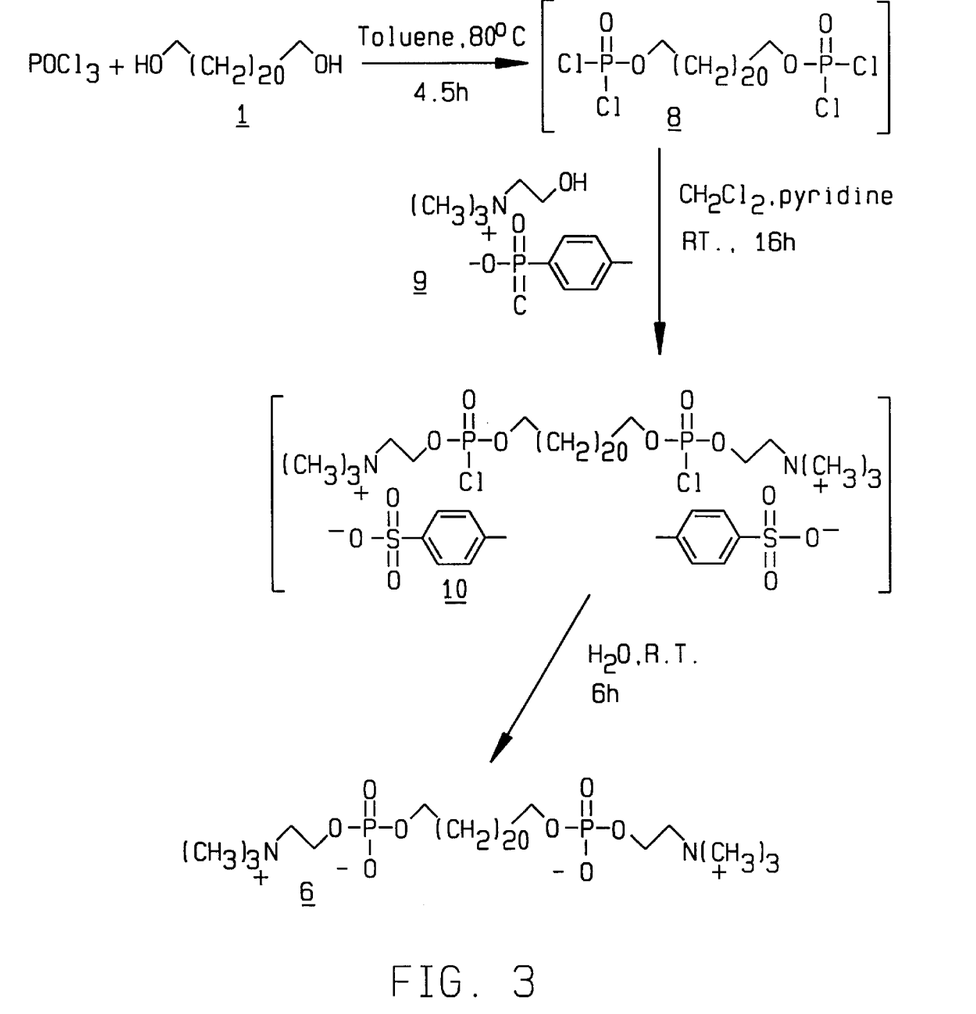
FIG. 3 schematically illustrates the direct one-pot phosphorylative synthetic process for obtaining a bis-phosphocholine according to the invention using the synthesis of 1,22-bis[2-(trimethylammonium)ethylphosphatyl] docosane as an illustrative example.

Alternatively, symmetrical bis(phosphocholine) derivatives X can be prepared more directly by simultaneous phosphorylation of VIII with an appropriate phosphorylating agent to provide bisphosphate IX. Bis phosphate IX can then be converted to the desired bis(phosphocholine derivative X. The parent symmetrical bisphosphocholine derivative $X[V_1=N(CH_3)_3]$ can be prepared from VIII in "one pot" using phosphorous oxychloride and choline tosylate. See, for example, FIG. 3.

For the stepwise process, the preferred reaction temperature is between about −20° to about 80° C., and more preferably between about 0° to about 50° C. For the one-pot process, the preferred reaction temperature is between about room temperature to about 120° C.

The reaction is preferably conducted under an inert atmosphere under atmospheric pressure.

The reaction solvent used must be a non-protic solvent and is preferably but not exclusively tetrahydrofuran, diethyl ether diisopropyl ether, t-butyl methyl ether, tert-butyl ethyl ether, ethylene glycol dimethyl ether, diethylene glycol dimethyl ether, dichloromethane, dichloroethane, chloroform, dimethylformamide, benzene, toluene, ethyl acetate, and mixtures thereof.

The more preferred solvent is diethyl ether, tetrahydrofuran, or dichloromethane.

A base is preferably used for the phosphorylating the bifunctional alcohol, thiol amine. The base is among but not exclusive to the following: triethylamine, diisopropylethylamine, diisopropylamine, N-methylmorpholine, pyridine, 2,6-lutidine, dimethylaminopyridine, morpholine, imidazole, and N-methylimidazole, with triethylamine, diisopropylethylamine, and N-methylmorpholine being preferred.

In removing the alcoholic protecting group of monophosphate XI where the group is a silicon based protecting group, the preferred pH of the reaction solvent is pH 4–8, and preferably between 5.5 and 7.

According to the methods of the invention, the preferred protecting groups for alcoholic functions are among but not exclusive to the following: acetate, benzoate, benzyl, benzylidene, isopropylidene, tert-butyldimethylsilyl, tert-butyldiphenylsilyl, allyl, methoxyethoxyethyl, triphenylmethyl, tetrahydropyranyl, diphenylmethyl, p-methoxybenzyl, 3,4-dimethoxybenzyl, p-toluenesulfonyl, benzenesulfonyl, tert-butyl, tert-butyloxymethyl, 2-(trimethylsilyl)ethoxymethyl, methoxymethyl, 2-(trimethylsilyl)ethyl, dimethylthexylsilyl, benzyloxymethyl, p-methoxybenzyloxymethyl, (4-methoxyphenoxy)methyl, methylthiomethyl, 2,2,2-trichloroethoxy-methyl, tribenzylsilyl, triphenylsilyl, diphenylmethylsilyl, and tert-butylmethoxyphenylsilyl.

According to the methods of the invention, the preferred protecting groups for nitrogen are among but not exclusive to the following: tert-butyloxycarbonyl, benzyloxycarbonyl, 9-phenylfluorenyl, allyloxycarbonyl, allyl, benzyl, triphenylmethyl, adamantyloxycarbonyl, 2,2,2-trichloroethyloxycarbonyl, 2-(trimethylsilyl) ethoxycarbonyl, p-toluenesulfonyl, benzylidene, diphenylmethyloxycarbonyl, 2-cyanoethyl, 2-cyanoethyloxycarbonyl, 9-fluorenylmethyloxycarbonyl, p-methoxybenzyloxycarbonyl, p-nitrobenzyloxycarbonyl, p-bromobenzyloxycarbonyl, benzenesulfonyl, toluenesulfonyl, p-chlorobenzyloxycarbonyl, o-nitrobenzyloxy-carbonyl, benzylidene, N-1,1-dithiomethylene, 2,3,6-trimethyl-4-methoxybenzenesulfonyl, benzylsulfonyl, 2,4,6-trimethoxybenzenesulfonyl, 2,4,6-trimethylbenzenesulfonyl, p-methoxybenzenesulfonyl, and 2-trimethylsilylethanesulfonyl.

According to the methods of the invention, the preferred protecting groups for carboxyl oxygen are among but not exclusive to the following: methyl, ethyl, isopropyl, t-butyl, diphenylmethyl, benzyl, 2-cyanoethyl, 2-trimethylsilylethyl, 2,2,2-trichloroethyl, tert-butyldimethylsilyl, tert-butyldiphenylsilyl, 2-(trimethylsilyl)ethoxymethyl, tribenzylsilyl, triphenylsilyl, diphenylmethylsilyl, tert-butylmethoxyphenylsilyl, p-methoxybenzyl, and phenacyl.

According to the methods of the invention, the preferred protecting groups for sulfur are among but not exclusive to the following: triphenylmethyl, tert-butyl, acetyl, benzyl, p-methoxybenzyl, p-nitrobenzyl, diphenylmethyl, 1-adamantyl, and 2-cyanoethyl.

5.2. COMPOUNDS

The methods described in Section 5.1 are advantageously used to synthesize the mono- and bis-phosphocholine derivatives described in Section 3 above.

5.3. METHODS OF USE

The phosphocholine derivatives described herein are all useful to treat fungal infections by administering, to a warm-blooded animal, a therapeutically effective amount of a pharmaceutical composition comprising a phosphocholine derivative. Fungal infections which can be treated include but are not limited to *Candida albicans, Crytococcus neoformans, Aspergillus fumagatus, Candida krusei, Candida parapsilosis, Candida tropicalis*, and *Trichophyton rubrum*. The pharmaceutical composition comprising the phosphocholine derivative used for such administration may also contain pharmaceutically acceptable excipients and carriers.

In order to treat a fungal infection, the antifungal agents described in this invention may be administered to a warm-blooded animal intravenously, intraperitoneally, subcutaneously, intramuscularly, orally, topically, by aerosol, or combinations thereof.

The antifungal agent of the phosphocholine derivatives described herein can be administered intravenously in a range of about 0.1 to about 10 mg/kg body weight.

The antifungal agent of the phosphocholine derivatives described herein can be administered intraperitoneally in a range of about 0.1 to about 10 mg/kg body weight.

The antifungal agent of the phosphocholine derivatives described herein can be administered subcutaneously in a range of about 1 to about 20 mg/kg body weight.

The antifungal agent of the phosphocholine derivatives described herein can be administered intramuscularly in a range of about 1 to about 20 mg/kg body weight.

The antifungal agent of the phosphocholine derivatives described herein can be administered orally in a range of about 5.0 to about 30 mg/kg body weight.

The antifungal agent of the phosphocholine derivatives described herein can be administered topically in a range of about 5.0 to about 15% by weight.

The antifungal agent of the phosphocholine derivatives described herein can be administered by aerosol in a range of about 5.0 to about 30 mg/kg/day.

In general, the pharmaceutical compositions or formulations are prepared by uniformly and intimately bringing into association the active ingredient with a liquid carrier or finely divided solid carrier or both, and then if necessary shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations suitable for topical administration include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered an a pharmaceutically acceptable carrier. A preferred topical delivery system is a transdermal patch containing the ingredient to be administered.

Formulations suitable for nasal administration wherein the carrier is a solid include a coarse powder having a particle size, for example, in the range 20 to 500 microns which is administered in the manner in which snuff is taken, i.e., by rapid inhalation through the nasal passage from a container of the powder held close up to the nose. Suitable formulations wherein the carrier is a liquid, for administration, as for example, a nasal spray or as nasal drops, include aqueous or oily solutions of the active ingredient.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient.

It should be understood that in addition to the ingredients particularly mentioned above the formulations of this invention may include other agents conventional in the art having regard to the type of formulation in question, for example, those suitable for oral administration may include flavoring agents.

The phosphocholines prepared by the method described in this invention are also useful as an active agent in a disinfectant or cleaning composition, which composition possesses fungicidal and/or fungistatic, antibacterial and/or antiviral properties.

The present invention may be more fully understood in light of the following examples which are presented by way of illustration and not by way of limitation.

6. EXAMPLES: SYNTHESIS OF PHOSPHOCHOLINES

6.1. GENERAL EXPERIMENTAL MATERIALS AND METHODS

Tetrahydrofuran (THF) was distilled from potassium/benzophenone; benzene, triethylamine, and methylene chloride, and benzyl alcohol were distilled from calcium hydride; 2-bromoethylphosphorodichloridate was prepared according to the procedure reported by Baumann et al., [Lipids, 17, 453, (1982)] and was freshly distilled prior to use. Anhydrous dimethylformamide (DMF) was obtained from Aldrich. 1,22-Docosanedioic acid was obtained from Fluka. Flash column chromatography was performed on Whatman 230–400 mesh silica gel using nitrogen pressure. $^1$H and $^{13}$C NMR were provided by the Shaman Pharmaceutical Physical Chemistry Department using a Varian 400 MHz spectrometer with chloroform as an internal reference unless otherwise noted. NMR shifts were expressed in ppm downfield from internal tetramethylsilane. NMR assignments were determined on the basis of COSY, HMQC, and HMBC and DEPT experiments performed on selected intermediates. NMR coupling constants are reported in Hertz. Mass spectrometry was performed by the Physical Chemistry Department at Shaman Pharmaceuticals, or by the Analytical Services Department and the University of California, Berkeley. Elemental analyses were performed by Analytical Services Department at the University of California, Berkeley. Melting points were determined using a Buchi model 535 melting point apparatus and are uncorrected.

6.2. EXAMPLES OF SYNTHESIS

EXAMPLE 1

1,22-Docosanediol 1

Docosanedioic acid (6.38 g, 17.2 mmol) was suspended in freshly distilled THF (300 mL) in a nitrogen-purged 500 mL three-necked flask fitted with a magnetic stirbar and thermometer. The solution was chilled to 2° C. and a solution of 1.0M borane in tetrahydrofuran (51.7 mL, 51.7 mmol) was slowly added. The mixture was stirred for 0.5 hours at 2° C. The reaction mixture was gradually warmed over a period of 3 hours to 45° C. at which point the white suspension became a clear homogenous solution. The mixture was gradually cooled down to room temperature over a period of 2 hours with the reaction mixture remaining clear and homogenous. To the reaction mixture was carefully added 2M NaOH (25.8 mL, 51.7 mmol) which caused a precipitation of a white solid. After stirring for 0.5 hours, hydrogen peroxide (5.85 g, 30 wt %, 56.7 mmol) was added to the stirring solution. After stirring for 0.5 h, the reaction mixture was diluted with ether (1 L) and washed with brine (2×200 mL). The ethereal layer was dried ($Na_2SO_4$) and concentrated while the aqueous portion was set aside. The solid white material was recrystallized twice from hot methanol to yield a fluffy white solid (1.24 g, 21% yield).

The previously saved aqueous portion contained a floating white emulsion. Extraction of the emulsion with 1:3 isopropanol/methylene chloride (400 mL) was unsuccessful in that it also extracted undesirable side products. The organic solvent was removed in vacuo and the isolated material was returned to the aqueous portion. The total aqueous portion was filtered, and the isolated solid material was washed with water (60 mL) and ether (20 mL). The solid material was recrystallized twice from hot methanol to yield a fluffy white solid (3.87 g, 66% yield). The isolated product from both pathways was combined to afford the desired diol 1 (5.10 g, 87% yield overall).

$^1$ NMR ($CDCl_3$, 60° C.) δ4.54 (2H, bm, OH), 3.54 (4H, t, J=6.8 $CH_2OH$), 1.53 (4H, p, J=7.2, $CH_2CH_2OH$), 1.29 (36H, s).

$^{13}$C NMR ($CDCl_3$, 60° C.) δ63.10 ($CH_2OH$), 33.67 ($CH_2CH_2OH$), 26.910 ($CH_2CH_2CH_2OH$), 30.52 ($CH_2(CH_2)_3OH$) 30.65.

EXAMPLE 2

1-tert-Butyldimethylsilyloxy 22-docosanol 2

1,22-Docosanediol 1 (2.00 g, 5.84 mmol) and imidazole (0.817 g, 12.0 mmol) were placed in each of two nitrogen-purged 150 mL three-necked flasks fitted with a thermometer and magnetic stir bar. The flasks were resealed and purged with nitrogen. Dimethylformamide (40 mL) was added to each flask and the cloudy mixtures were heated until they became homogenous at 63° C. tert-Butyldimethylsilyl chloride (0.904 g, 6.00 mmol, in 10 mL DMF) was slowly added to the reaction mixture (the transfer was aided with an additional 5 mL of DMF) and the mixture was allowed to react for 24 hours at 60°–65° C. The solutions were cooled down to room temperature and filtered to recover starting material using water (25 mL) to aid in transfer. The filtrate was diluted with water (300 mL) and extracted with methylene chloride (500 mL). The organic layer was dried ($Na_2SO_4$) and concentrated. A very low mass balance led to the discovery that much of the desired material was contained in the recovered solid that had been previously filtered off. None of the desired compound was found in the aqueous wash by TLC. The recovered solid was suspended in methylene chloride (100 mL), stirred, and refiltered. The filtrate was combined with the previously isolated material and concentrated in vacuo. The crude material was purified by flash chromatography (silica gel, 10% ethyl acetate/hexane). Concentration of the desired fractions using acetone to reduce violent bumping yielded the desired material 2 as a white solid (2.22 g, 46.7%).

$^1$H NMR ($CDCl_3$) δ3.63 (2H, t, J=6.6, $CH_2OH$), 3.59 (2H, t, J=6.6, $CH_2OSi$), 1.57–1.48 (5H, multiplet including singlet for $CH_2OH$ at 5.29 ppm ($CH_2CH_2OH/CH_2CH_2OSi$), 1.25 (36H, s, $CH_2(CH_2)_{18}CH_2$), 0.89 (9H, s, $SiCCH_3$), 0.04 (6H, s, $SiCH_3$).

$^{13}$C NMR ($CDCl_3$) δ63.35 ($CH_2OH$), 63.07 ($CH_2OSi$), 32.87 ($CH_2CH_2OH$), 32.80 ($CH_2CH_2OSi$), 29.67, 29.60, 29.43, 25.96 ($SiC(CH_3)$), 25.78 ($CH_2(CH_2)_2OH$), 25.72 ($CH_2(CH_2)_2OSi$), 18.3 ($SiC(CH_3)$), −5.29 ($SiCH_3$).

EXAMPLE 3

1-[Benzyl (2-bromoethyl) phosphatyl]-22-[tert-butyldimethylsilyloxy]docosane 3

In a dry, nitrogen-purged three-necked flask fitted with a magnetic stir bar and thermometer was placed dry diethyl ether (400 mL) and freshly distilled 2-bromoethylphosphorodichloridate (6.67 g, 27.6 mmol). The mixture was cooled down to 1° C. and recently distilled triethylamine (31.4 mL, 225 mmol) was added causing a white precipitate to form. After 0.5 hours, a solution of 1-t-butyldimethylsilyloxy-22-docosanol 2 (2.22 g, 4.87 mmol, in 10 mL diethyl ether) was added to the stirring solution. The reaction mixture was gradually warmed to room temperature and allowed to stir for 16 hours after which benzyl alcohol (4.76 mL, 46.0 mmol) was added and the solution stirred for an additional 24 hours. The organic phase was filtered off, using ether (60 mL) to aid in the transfer, and concentrated in vacuo. The crude material was purified by flash chromatography (silica gel, 25% ethyl acetate/hexane) to afford product 3 as a light yellow oil (0.902 g, 26.7%).

$^1$H NMR ($CDCl_3$) δ7.37 (m, 5H), 5.09 (d, 2H, J=8.40, $CH_2Ph$), 4.28–4.16 (bm, 2H, $BrCH_2CH_2O$), 4.03 (dd, 2H, J=6.8, J=6.8, $CH_2OP$), 3.59 (t, 2H, J=6.4, $BrCH_2CH_2O$), 3.46 (t, 2H, J=6.4, $CH_2OSi$), 1.64 (p, 2H, J=6.8), 1.50 (p, 2H, J=6.4), 1.25 (bs, 36H), 0.89 (s, 9H), 0.04 (s, 6H).

$^{13}$C NMR ($CDCl_3$) δ two carbons missing, 128.61, 127.98, 69.44 (d, J=6.1), 68.33 (d, J=6.0), 66.53 (d, J=5.3), 63.33 ($CH_2OSi$), 32.90 ($CH_2CH_2OH$), 30.19 ($CH_2CH_2OP$), 29.69, 29.63, 29.61, 29.55, 29.48, 29.44, 29.34 (d, ($CH_2CH_2Br$), 29.10, 25.98 (($CH_3)_3C$), 25.81 ($CH_2(CH_2)_2OH$), 25.38 ($CH_2(CH_2)_2OP$), 18.35 $SiC(CH_3)_3$), −5.26 ($SiC(CH_3)_3$).

$^{31}$P NMR ($CDCl_3$) δ−0.80.

EXAMPLE 4

22-[Benzyl (2-bromoethyl) phosphatyl]-docosan-1-ol 4

To a stirring solution of the silyl phosphate 3 (0.870 g, 1.19 mmol) in dry THF (40 mL) was slowly added dropwise a premixed solution of tetrabutylammonium fluoride (11.9 mL, 11.9 mmol) and glacial acetic acid (6.8 mL, 119 mmol). After stirring for 16 hours, the mixture was diluted with methylene chloride (200 mL) and washed with 1M disodium phosphate solution (2×100 mL) at which point the organic phase appeared neutral by pH paper. The organic phase was dried ($MgSO_4$) and concentrated in vacuo. The crude material was purified by flash chromatography (silica gel, 25% ethyl acetate/hexane) to yield the desired phosphate alcohol 4 (0.452 g, 62%

$^1$H NMR (CDCl$_3$) δ7.42–7.35 (bm, 5H), 5.10 (d, 2H, J=8.8, CH$_2$Ph), 4.26 (bm, 2H, BrCH$_2$CH$_2$O), 4.04 (dd, 2H, J=6.8, CH$_2$OP), 3.65 (t, 2H, J=6.8, BrCH$_2$CH$_2$O), 3.48 (t, 2H, J=6.8, CH$_2$OH), 1.7–1.5 (m with pentet at 1.65 ppm, 5H, CH$_2$CH$_2$OP, CH$_2$CH$_2$OH, OH), 1.26 (bs, 36H).

$^{13}$C NMR (CDCl$_3$) δ132.5, 128.62, 127.98, 127.3, 69.45 (d, J=5.3), 68.36 (d, J=6.1), 66.55 (d, J=5.3), 63.09 (CH$_2$OH), 32.84 (CH$_2$CH$_2$OH), 30.20 (d, J=6.9, CH$_2$CH$_2$OP), 29.67, 29.60, 29.59, 29.55, 29.48, 29.43, 29.11, 25.75 (CH$_2$CH$_2$CH$_2$OH), 25.39 (CH$_2$CH$_2$CH$_2$OP).

$^{31}$P NMR (CDCl$_3$) δ–0.72.

EXAMPLE 5

1,22-Bis [benzyl (2-bromoethyl) phosphatyl] docosane 5

In a dry, nitrogen-purged three-necked flask fitted with a magnetic stir bar and thermometer was placed dry diethyl ether (20 mL) and freshly distilled 2-bromoethyl phosphorodichloridate (1.06 g, 4.38 mmol). The mixture was cooled down to 1° C. and freshly distilled triethylamine (5.0 mL, 35.8 mmol) was added causing a white precipitate to form. After 0.5 hours, a solution of the phosphate alcohol 4 (0.452 g, 0.730 mmol, in 10 mL diethyl ether) was added to the stirring solution. The ice bath was removed and the mixture was allowed to stir for 1.5 hours until the starting alcohol 4 appeared consumed by TLC. Benzyl alcohol (0.75 mL, 7.30 mmol) was added and the solution stirred for 16 hours. The mixture was concentrated in vacuo, homogenized using ethanol (10 mL), precipitated using ether, filtered, and re-concentrated. The crude material was purified by flash chromatography (silica, 25% ethyl acetate/hexane gradiated to 100% ethyl acetate). The desired fractions were concentrated to afford a yellow oil (0.203 g, 31%) which, under certain TLC conditions, separates into two spots of equal intensity to phosphomolybdic acid stain.

$^1$H NMR (CDCl$_3$) δ7.44–7.32 (m, 10H), 5.10 (d, 4H, J=8.8), 4.34–3.96 [m containing dd at 4.25 (4H, J=6.0, J=6.0), a dd at 4.03 ppm (4H, J=6.8, J=6.8), and an impurity; 11.6H total integration], 3.55–3.4 {two triplets, 5H integration total [one triplet at 3.54 (1H, J=6.4, impurity) and one triplet at 3.47 (4H, J=6.4)]}, 1.72–1.5 (m, 12.5H total), 1.4–1.14 (bm, 51.6H total).

$^{13}$C NMR (CDCl$_3$) δ two carbons missing, 128.62, 127.98, 69.45 (d, J=5.3), 68.35 (d, J=6.0), 66.52 (t, J=6.1), 30.21 (d, J=6.8, CH$_2$CH$_2$OP), 29.71, 29.70, 29.64, 29.56, 29.49, 29.11, 25.39 (CH$_2$CH$_2$CH$_2$OP).

$^{31}$P NMR (CDCl$_3$) δ0.71.

EXAMPLE 6

1,22-Bis [2-(trimethylammonium)ethylphosphatyl] docosane (SP-19502) 6

A solution of the bis-phosphate 5 (0.202 g, 0.225 mmol) in dry THF (10 mL) was placed in a steel bomb fitted with a magnetic stir bar. To the solution was added freshly condensed trimethylamine (5 mL, 55.5 mmol). The bomb was sealed and heated to 50° C. for 16 hours. The bomb was cooled, opened, and allowed to stand open to atmosphere for 4 hours. The mixture was transferred from the bomb using THF and concentrated in vacuo to yield a yellow oil. The crude material was and purified using a HP-20 column (150 mL of Dianion High Porosity styrene and divinylbenzene copolymer –20 from Mitsubishi Chemical Industries Limited suspended in water, washed with 100% methanol, and re-equilibrated with water). The column was eluted with 750 mL of water, 500 mL water/methanol 1/1, and 500 mL 100% methanol under 4 psi nitrogen. Purification was monitored using amino-functionalized silica-bonded phase TLC plates which were visualized with a solution of 5% sulfuric acid in ethanol and prolonged heating. The material which co-spotted with the isolated natural product was found in the 100% methanol fraction. No product which could be visualized using the amino plates was found in either of the first two fractions. The 100% methanol fraction was concentrated to yield the desired compound 6 as a highly impure yellow oil (0.1357 g, 89.6%).

The semi-crude material was further purified using a Rainin HPLC system equipped with an amino-silica column (Microsorb NH$_2$80-799-C5) and a Perkin-Elmer RI detector (Range—0.050, Response time—0.5). The column was eluted with an isochratic system of degassed 3/1 isopropanol/water at a flow rate of 2 ml per minute and a pressure of 2900 psi. Yield=26.7 mg (17.6%).

$^1$H NMR (CD$_3$OD) δ4.25 (bm, 4H, (CH$_3$)$_3$N$^+$CH$_2$CH$_2$O), 3.87 (dd, 4H, J=6.4, J=6.4, CH$_2$OP), 3.63 (bt, 4H, J=4.8, (CH$_3$)$_3$N$^+$CH$_2$CH$_2$O), 3.22 (s, 18H, N$^+$(CH$_3$)$_3$), 1.63 (p, 4H, CH$_2$CH$_2$OP), 1.44–1.24 (bs at 1.29 with shoulder at 1.44–1.35, 36H).

$^{13}$C NMR (CD$_3$OD) δ67.54 (bm), 66.97 (d, J=6.1), 60.29 (d, J=4.62), 54.73 (t, J=3.82), 31.89 (d, J=7.6), 30.79, 30.49, 26.95.

$^{31}$P NMR (CD$_3$OD) δ1.34.

EXAMPLE 7

1,22-Bis [2-(trimethylammonium)ethylphosphatyl] docosane (SP-19502) 6.

To freshly distilled phosphorous oxychloride (0.45 mL, 4.86 mmol) stirring in dry toluene (25 mL) in a nitrogen-purged flask was directly added docosanediol 1 (0.500 g, 1.46 mmol). The flask was fitted with a condenser and purged with nitrogen. The white suspension became a clear homogenous solution upon heating. The mixture was allowed to stir for 4.5 h at 80° C. oil bath temperature. The mixture was cooled to room temperature, concentrated, and placed under high vacuum with mild heating until the grey, flaky residue appeared dry. To the dry residue dissolved in freshly distilled methylene chloride (20 mL) was added pyridine (1.5 mL, 19.9 mmol) and choline tosylate 7 (1.79 g, 6.48 mmol). The flask was purged with nitrogen and allowed to stir at room temperature for 16 h. During this period the mixture went from a viscous white suspension to a clear solution containing a quantity of white solid material. To the reaction mixture was added water (1.5 mL, 83.2 mmol) which was allowed to react for 6 h. The reaction mixture was concentrated in vacuo.

The crude material was dissolved in water (35 mL) and purified using a HP-20 column (150 mL of Dianion High Porosity styrene and divinylbenzene copolymer –20 from Mitsubishi Chemical Industries Limited suspended in water, washed with 100% methanol, and re-equilibrated with water. The column was eluted with 750 mL of water, 500 mL water/methanol 1/1, and 500 mL 100% methanol under 4 psi nitrogen. Purification was monitored using amino-functionalized silica-bonded phase TLC plates. The material which co-spotted with the isolated natural product was found in the 100% methanol fraction. No product which could be visualized using the amino plates was found in either of the first two fractions). The 100% methanol fraction was concentrated in vacuo and placed under high vacuum for 2 days to yield a waxy, yellow material (0.585 g, 59.8%).

A portion of the purified material was further purified using a Rainin HPLC system equipped with an amino-silica column (Microsorb NH$_2$80-799-C5) and a Perkin-Elmer RI detector (Range—0.050, Response time—0.5). The column was eluted with an isochratic system of degassed 3/1 isopropanol/water at a flow rate of 2 ml per minute and a pressure of 2,700 psi. The retention time of a 200 ml injection of a 33 mg/ml solution was 33.2 minutes. Sufficient material of the desired compound 6 was purified in this manner for spectroscopic analysis.

$^1$H NMR (CD$_3$OD) δ4.25 (bm, 4H, (CH$_3$)$_3$N$^+$CH$_2$CH$_2$O), 3.87 (dd, 4H, J=6.4, J=6.4, CH$_2$OP), 3.63 (bt, 4H, J=4.8, (CH$_3$)$_3$N$^+$CH$_2$CH$_2$O), 3.22 (s, 18H, N$^+$(CH$_3$)$_3$), 1.63 (p, 4H, CH$_2$CH$_2$OP), 1.44–1.24 (bs at 1.29 with shoulder at 1.44–1.35, 36H).

$^{13}$C NMR (CD$_3$OD) δ67.54 (bm), 66.97 (d, J=6.1), 60.29 (d, J=4.62), 54.73 (t, J=3.82), 31.89 (d, J=7.6), 30.79, 30.49, 26.95.

$^{31}$P NMR (CD$_3$OD) δ1.34.

7. ANTIFUNGAL ACTIVITY

The antifungal activity of two exemplary phosphocholines prepared using the method of the invention, i.e., (1) synthetic 1,22-Bis-[2-(trimethylammonium) ethylphosphatyl] docosane obtained using the stepwise synthetic route and, (2) synthetic 1,22-Bis-[2-(trimethylammonium)ethyl-phosphatyl] docosane obtained using the one-pot one step route, as well as the antifungal activity of (3) the natural product isolated from Irbachia alata identified as 1,22-Bis-[2-(trimethylammonium)ethyl-phosphatyl] docosane (see International Application filed Oct. 8, 1993 was determined in vitro using three fungal cultures—*Candida albicans* (CA), *Cryptococcus neoformans* (CN), and *Aspergillus fumigatus* (CF). The method used to determine in vitro antifungal activity is described in McGinnis, M. R., *Laboratory Handbook of Medical Mycology*, Academic Press, New York, London, p 412–416 (1980); and Drouget, E.; Dupont, B.; Improvisi, L.; Vivian, M. A.; and Tortorano, A. M.; "Disc agar difusion and microplate automatized techniques for in vitro evaluation of antifungal agents on yeast and sporulated pathogenic fungi" in In Vitro and In Vivo Evaluation of Antifungal Agents, Eds. Iwata, K. and Vanden Bossche, H., Elsevier Science Publishers, New York, Oxford, p 303 (1986). The minimum inhibitory concentration (MIC) for each is summarized in Table I. Partial inhibition of the fungus of between 25% to 75% was also measured. A description of the partial inhibition measurement can be found in R. L. Stiller, et al, *The Journal of Infectious Diseases*, 147, No 6 (1983). The data relating to partial inhibition are also presented in Table I.

TABLE I

Antifungal Activity of Phosphocholine Derivatives

| Phosphocholine Derivative | MIC (μg/ml) | | | Partial inhibition (μg/ml) | | |
|---|---|---|---|---|---|---|
| | CA | CN | AF | CA | CN | AF |
| Synthetic 1,22-Bis[2-trimethyl-ammonium)ethyl phosphatyl] docosane | 1.25 | 0.08 | 0.08 | n/a | n/a | 0.02 |
| Synthetic 1,22-Bis[2-(trimethyl-ammonium)ethyl phosphatyl] docosane (one pot process) | 0.8 | <0.1 | <0.1 | n/a | n/a | 0.1 |
| Isolated Natural Product 1,22-Bis[2[(trimethyl-ammonium)ethyl phosphatyl] docosane | 1.25 | <0.04 | 0.08 | n/a | n/a | n/a |

CA refers to *Candida albicans*

CN refers to *Cryptococcus neoformans*

AF refers to *Aspergillus fumigatus* n/a refers to no data available

The results indicate that the antifungal activities of the natural product and that of the products of the two synthetic routes are essentially the same. Effective antifungal activity for the purposes of the present invention is defined as a MIC of less than or equal to about 500 μg/ml for CA, CN or AF.

All references cited in the present application are incorporated by reference in their entirety.

The invention described and claimed herein is not to be limited in scope by the specific embodiments herein disclosed since these embodiments are intended as illustration of several aspects of the invention. Any equivalent embodiments are intended to be within the scope of this invention. Indeed, various modifications of the invention in addition to those shown and described herein will become apparent to those skilled in the art form the foregoing description. Such modifications are also intended to fall within the scope of the appended claims.

What is claimed:

1. A method of synthesizing a compound having a phosphocholine group, comprising the steps of:
   (a) phosphorylating a hydroxyl, sulfhydryl or amino group of a starting material with an alkyl phosphorodichloridate having a leaving group in the ω-position of said alkyl to obtain a phosphorochloridate intermediate;
   (b) reacting the phosphorochloridate intermediate with benzyl alcohol or phenol to obtain an aryl(alkyl) phosphatidyl intermediate having a leaving group in the ω-position of said alkyl; and
   (c) reacting the aryl(alkyl)phosphatidyl intermediate with an amine to obtain the compound having a phosphocholine group.

2. The method according to claim 1, in which said starting material has two functional groups selected from the group consisting of hydroxyl, sulfhydryl and amino, wherein one of said functional groups is protected with a protecting group, the protecting group for the hydroxyl group being selected from the group consisting of acetate, benzoate, benzyl, benzylidine, isopropylidine, tert-butyldimethylsilyl, tert-butyldiphenylsilyl, allyl, methoxyethoxyethyl, triphenylmethyl, tetrahydropyranyl, diphenylmethyl, p-methoxybenzyl, 3,4-dimethoxybenzyl, p-toluenesulfonyl, benzenesulfonyl, tert-butyl, tert-butyloxymethyl, 2-(trimethylsilyl)ethoxymethyl, methoxymethyl, 2-(trimethylsilyl)ethyl, dimethylthexylsilyl, benzyloxymethyl, p-methoxybenzyloxymethyl, (4-methoxyphenoxy)methyl, methylthiomethyl, 2,2,2-trichloroethoxymethyl, tribenzylsilyl, triphenylsilyl, diphenylmethylsilyl, and tert-butylmethoxyphenylsilyl;

the protecting group for the amino group being selected from the group consisting of tert-butyloxycarbonyl, benzyloxycarbonyl, 9-phenylfluorenyl, allyloxycarbonyl, allyl, benzyl, triphenylmethyl, adamantyloxycarbonyl, 2,2,2-trichloroethyloxycarbonyl, 2-(trimethylsilyl)ethoxycarbonyl, p-toluenesulfonyl, benzylidine, diphenylmethyloxycarbonyl, 2-cyanoethyl, 2-cyanoethyloxycarbonyl, 9-fluorenylmethyloxycarbonyl, p-methoxybenzyloxycarbonyl, p-nitrobenzyloxycarbonyl, p-bromobenzyloxycarbonyl, benzenesulfonyl, toluenesulfonyl, p-chlorobenzyloxycarbonyl, o-nitrobenzyloxy-carbonyl, benzylidine, N-1,1-dithiomethylene, 2,3,6-trimethyl-4-methoxybenzenesulfonyl, benzylsulfonyl, 2,4,6-trimethoxy-benzenesulfonyl, 2,4,6-trimethylbenzenesulfonyl, p-methoxybenzenesulfonyl, and 2-trimethylsilylethanesulfonyl; and the protecting group for the sulfhydryl group being selected from the group consisting of triphenylmethyl, tert-butyl, acetyl, benzyl, p-methoxybenzyl, p-nitrobenzyl, diphenylmethyl, 1-adamantyl, and 2-cyanoethyl.

3. The method of claim 1, wherein the alkyl phosphorodichloridate is a phosphorylating agent of type where $F_1$ is defined as a $C_2$–$C_{10}$ alkyl group; and $E_1$ is a leaving group selected from the group consisting of benzenesulfonyl, pentafluorobenzenesulfonyl, toluenesulfonyl, p-nitrobenzenesulfonyl, p-bromobenzenesulfonyl, p-chlorobenzenesulfonyl, p-iodobenzenesulfonyl, p-fluorobenzenesulfonyl, 2,4,6-trimethylbenzenesulfonyl, 2,4,6-triisopropylbenzenesulfonyl, methanesulfonyl, trifluoromethanesulfonyl, Br, Cl, I, and F.

4. The method according to claim 3, wherein the starting material is a bifunctional molecule Y—Q—X, wherein X and Y are independently oxygen, sulfur, or $NR_{15}$, where $R_{15}$ is hydrogen, an alkyl radical having 1 to 6 carbon atoms, phenyl, phenylmethyl, or a protecting group; and Q is a linking spacer moiety selected from the group consisting of alkyl, alkenyl, alkynyl, heteroalkyl, aromatic and heteroaromatic rings.

5. The method according to claim 4, wherein the amine is of the formula $NR_{47}R_{48}R_{49}$, where each of $R_{47}$, $R_{48}$, and $R_{49}$ is independently hydrogen or an alkyl radical of C1 to C20 chain length which optionally possess 1 to 4 olefin or alkynyl unsaturation units, or mixtures or combinations thereof; where each of $R_{47}$ and $R_{48}$ is independently part of a ring containing 2 to 8 carbon atoms, or part of an aromatic or heteroaromatic; or where each of $R_{47}$, $R_{48}$, and $R_{49}$ is independently part of a bridged alkyl ring; or $R_{49}$ is:

—$(CH_2)_{d_1}$—$R_{50}$ or hydrogen, where $d_1$=0 to 20 and where $R_{50}$ is defined as hydrogen, a cycloalkyl radical of 3 to 8 carbon atoms, an aryl radical, a pyridyl radical, a furanyl radical, a thiophenyl radical, or a pyrollyl radical, or when $d_1 \neq 0$ or 1, then $R_{50}$ is SH, $SO_3H$, $SO_3^-$, COOH, $COO^-$, $NH_2$, $NH_3^+$, or OH.

6. A method for synthesizing a compound having a phosphocholine group, comprising the steps of:

(a) reacting PG—X—Q—Y wherein X and Y are independently oxygen, sulfur, or $NR_{15}$, where $R_{15}$ is hydrogen, an alkyl radical having 1 to 6 carbon atoms, phenyl, phenylmethyl, or a protecting group; and Q is a linking spacer moiety selected from the group consisting of alkyl, alkenyl, alkynl, heteroalkyl, aromatic and heteroaromatic rings, and PG is a protecting group, with a phosphorylating agent of type to afford a phosphorochloridate intermediate, wherein $F_1$ is a $C_2$–$C_{10}$ alkyl group and $E_1$ is a leaving group selected from the group consisting of benzenesulfonyl, pentafluorobenzenesulfonyl, toluenesulfonyl, p-nitrobenzenesulfonyl, p-bromobenzenesulfonyl, p-chlorobenzenesulfonyl, p-iodobenzenesulfonyl, p-fluorobenzenesulfonyl, 2,4,6-trimethylbenzenesulfonyl, 2,4,6-triisopropylbenzenesulfonyl, methanesulfonyl, trifluoromethanesulfonyl, Br, Cl, I, and F;

(b) reacting the phosphorochloridate intermediate with $R_{300}OH$, where $R_{300}$ is phenyl or benzyl, to form

(c) removing the protecting group PG from the product of step (b);

(d) phosphorylating the X functional group of the product of step (c) with a phosphorylating agent of type and (e) reacting the product of step (d) with $R_{300}OH$ to form 7. The method of claim 6 further comprising the step of (f) reacting the product of step (e) with an amine, so as to displace the leaving groups $E_1$ sequentially or simultaneously therefrom; wherein the amine is of the formula $NR_{47}R_{48}R_{49}$, where $R_{47}$, $R_{48}$, and $R_{49}$ are independently hydrogen or alkyl radicals of C1 to C20 chain length which optionally possess 1 to 4 olefin or alkynyl unsaturation units, or mixtures or combinations thereof; where $R_{47}$ and $R_{48}$ are part of a ring containing 2 to 8 carbon atoms, or part of an aromatic or heteroaromatic; or where $R_{47}$, $R_{48}$, and $R_{49}$ are part of a bridged alkyl ring; or $R_{49}$ is:

—$(CH_2)_{d1}$—$R_{50}$ or hydrogen [nil], where $d_1$=0 to 20 and where $R_{50}$ is defined as hydrogen, a cycloalkyl radical of 3 to 8 carbon atoms, an aryl radical, a pyridyl radical, a furanyl radical, a thiophenyl radical, or a pyrollyl radical, or when $d_1 \neq 0$ or 1, then $R_{50}$ is SH, $SO_3H$, $SO_3^-$, COOH, $COO^-$, $NH_2$, $NH_3^+$, or OH.

8. The method according to claim 6 where the $E_1$ groups of the phosphorylating agents of steps (a) and (d) are identical, and the $F_1$ groups of the phosphorylating agents of steps (a) and (d) are identical.

9. The method according to claim 6 where the $E_1$ groups of the phosphorylating agents of steps (a) and (d) are not identical, and the $F_1$ groups of the phosphorylating agents of steps (a) and (d) are identical.

10. The method according to claim 6 where the $E_1$ groups of the phosphorylating agents of steps (a) and (d) are identical, and the $F_1$ groups of the phosphorylating agents of steps (a) and (d) are not identical.

11. The method according to claim 6 where the $E_1$ groups of the phosphorylating agents of steps (a) and (d) are not identical, and the $F_1$ groups of the phosphorylating agents of steps (a) and (d) are not identical.

12. A method of synthesizing a compound having a phosphocholine group, comprising the steps of:

(a) reacting a starting material having a hydroxyl group with 2-bromoethylphosphorodichloridate to afford an alkyl phosphorochloridate intermediate;

(b) reacting the alkyl phosphorochloridate intermediate with benzyl alcohol or phenol to afford a phosphatidyl intermediate; and (c) reacting the phosphatidyl intermediate with a trialkylamine to afford the compound having a phosphocholine group.

13. The method of claim 12, wherein the starting material is a primary alcohol and the trialkylamine is trimethylamine.

14. A method for synthesizing a bis(phosphocholine) compound, comprising the steps of:

(a) reacting an $\alpha,\omega$-diol with 2-bromoethylphosphorodichloridate to afford a silyloxy monophosphorochloridate intermediate, said $\alpha,\omega$-diol having a protecting group on one of said $\alpha$- or $\omega$-hydroxyl groups, said protecting group is selected from the group consisting of tert-butyldimethylsilyl, tert-butyldiphenylsilyl, dimethylthexylsilyl, tribenzylsilyl, triphenylsilyl, diphenylmethylsilyl and tert-butylmethoxyphenylsilyl;

(b) reacting the silyloxy monophosphorochloridate intermediate with benzyl alcohol or phenol to afford a silyloxy monophosphatidyl intermediate;

(c) reacting the silyloxy monophosphatidyl intermediate with fluoride to afford a hydroxy monophosphatidyl intermediate;

(d) reacting the hydroxy monophosphatidyl intermediate with 2-bromoethylphosphorodichloridate to afford a bis(phosphorochloridate) intermediate;

(e) reacting the bis(phosphorochloridate) intermediate with benzyl alcohol or phenol to afford a bis (phosphatidyl) intermediate; and (f) reacting the bis(phosphatidyl) intermediate with a trialkylamine to afford the bis(phosphocholine) compound.

15. The method of claim 14, wherein the trialkylamine is trimethylamine.

* * * * *